United States Patent [19]

Manfre et al.

[11] 4,308,395

[45] Dec. 29, 1981

[54] PROCESSES FOR PREPARING 3,5,6-TRICHLOROSALICYLIC ACID AND ESTERS THEREOF

[75] Inventors: Robert J. Manfre; Arthur G. Mohan, both of Somerville; Michael M. Rauhut, Bridgewater, all of N.J.

[73] Assignee: American Cyanamid Company, Stamford, Conn.

[21] Appl. No.: 167,570

[22] Filed: Jul. 11, 1980

[51] Int. Cl.$^3$ ...................... C07C 69/76; C07C 65/00
[52] U.S. Cl. ....................................... 560/65; 562/474
[58] Field of Search ........................... 560/65; 562/474

[56] References Cited

U.S. PATENT DOCUMENTS 3,013,055 12/1961 Richter ................................ 562/474
3,210,414 10/1965 Hanna ................................. 562/474

*Primary Examiner*—Paul J. Killos
*Attorney, Agent, or Firm*—Gordon L. Hart

[57] ABSTRACT

An improved single-pot process for synthesis of 3,5,6-trichlorosalicylic acid and esters thereof is described. Salicylic acid is chlorinated first in concentrated sulfuric acid and then with iodine catalyst to make the trichlorosalicylic acid which is extracted and then reacted with an alcohol to make the ester.

6 Claims, No Drawings

PROCESSES FOR PREPARING 3,5,6-TRICHLOROSALICYLIC ACID AND ESTERS THEREOF

The use of 3,5,6-trichlorosalicylic acid as an intermediate in the preparation of n-pentyl 3,5,6-trichlorosalicylate was described by Rauhut in Example XXVI of U.S. Pat. No. 3,749,679. The latter compound is an intermediate in the preparation of bis(2,4,5-trichloro-6-carbopentoxyphenyl)oxalate which is useful in chemiluminescent compositions, as described in U.S. Pat. Nos. 3,597,362; 3,781,329; and 3,816,326.

The preparation of 3,5,6-trichlorosalicyclic acid in the prior art is carried out by chlorinating 3,5-dichlorosalicyclic acid in fuming sulfuric acid containing a catalytic amount of iodine at about 70° C. for a period of 2 hours, as described by Hanna in U.S. Pat. No. 3,062,877, to obtain a 92.4% yield of the desired product.

The preparation of 3,5-dichlorosalicylic acid, as disclosed by Leulier and Pinet, Bull. Soc. Chim. 41, 1362-1370 (1927), by reacting salicyclic acid with hydrogen chloride in perhydrol, affords an 80% yield of the desired product.

Thus, the overall yield of 3,5,6-trichlorosalicylic acid from salicylic acid by the combination of the above references is about 74%.

Richer disclosed in U.S. Pat. No. 3,013,055 the preparation of 3,5-dichlorosalicylic acid by chlorinating salicylic acid with chlorine gas in glacial acetic acid, isolating the 3,5-dichlorosalicylic acid and further chlorinating this material at 80°-90° C. in fuming sulfuric acid. The reaction mixture is cooled, poured on ice and extracted with diethyl ether to obtain 3,5,6-trichlorosalicylic acid in an overall yield of 52.5% based on salicylic acid.

Rauhut also discloses in Example XXVI of U.S. Pat. No. 3,749,679 the conversion of 3,5,6-trichlorosalicylic acid to the n-pentyl ester by refluxing it in n-pentyl alcohol containing a catalytic amount of sulfuric acid. The product is obtained in a yield of about 73% of theoretical. The combination of Hanna, Leulier and Pinet, and Rauhut indicates an overall yield for the preparation of the n-pentyl ester of about 53% of theoretical.

There is a need, therefore, for processes that produce significantly higher yields of 3,5,6-trichlorosalicylic acid and esters thereof.

In accordance with the present invention, salicylic acid is treated with gaseous chlorine in concentrated sulfuric acid to form 3,5-dichlorosalicylic acid. This product is converted by further chlorination in oleum, containing iodine, at about 40°-60° C., to 3,5,6-trichlorosalicylic acid, which is recovered by drowning the reaction mixture on ice and water, whereupon the product precipitates as a solid. The 3,5,6-trichlorosalicylic acid precipitate can be extracted from the drowned reaction mixture by mixing in a water-immiscible aromatic hydrocarbon solvent at a temperature of at least 60° C., and separating the organic phase, which contains the 3,5,6-trichlorosalicyclic acid. Xylene is a preferred immiscible solvent for this purpose.

In accordance with the present invention, there is also provided a process for preparing esters of 3,5,6-trichlorosalicylic acid represented by formula (I)

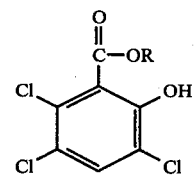

in which R represents alkyl ($C_3$-$C_{20}$). A solution of 3,5,6-trichlorosalicylic acid is prepared as described above, by extracting the drowned reaction mixture with a mixture of water-immiscible aromatic hydrocarbon solvent and an alcohol ($C_3$-$C_{20}$). This mixture is treated with a catalytic amount of a suitable acid, and heated at an elevated temperature to evaporate the water-alcohol azeotrope from the solution which contains the compound of formula (I), in the immiscible organic solvent.

In one especially preferred embodiment, the water-immiscible hydrocarbon solvent is xylene, the extraction is at 75°-100° C., the alcohol is n-pentanol, and the acid catalyst is concentrated sulfuric acid.

Some advantages of the present invention are as follows:

1. The 3,5,6-trichlorosalicylic acid is obtained in very high purity, about 99%, and in a relatively high yield.

2. The 3,5,6-trichlorosalicylic acid can be prepared directly from salicylic acid by a series of steps which can all be performed in a single reaction vessel.

3. The ester of 3,5,6-trichlorosalicylic acid can also be obtained in a very high yield and purity, without the need for isolating the 3,5,6-trichlorosalicylic acid. The overall yield from salicylic acid to n-pentyl 3,5,6-trichlorosalicylate is about 92-95% of theoretical; the purity of the product is about 98%.

4. Recovery of the 3,5,6-trichlorosalicylic acid precipitate by extraction from water with a water-immiscible aromatic solvent containing a suitable alcohol results in a 10-15% increase in the final yield of the product of formula (I).

In carrying out the preparation of 3,5,6-trichlorosalicylic acid, gaseous chlorine is passed into a vigorously stirred solution of salicylic acid in concentrated sulfuric acid, preferably 96-98% sulfuric acid, at a temperature below 35° C., preferably about 5°-10° C., until essentially all of the salicylic acid is converted to a monochlorosalicyclic acid. The mixture of 3-, and 5-chlorosalicyclic acids is then further converted to 3,5-dichlorosalicyclic acid by chlorination at a temperature of about 50°-75° C., preferably 65°-70° C. The stirring should be just vigorous enough to permit rapid reaction. Optionally, the chlorination may be carried out under pressure to increase the rate of reaction. Completion of the formation of the monochlorosalicylic acid and the 3,5-dichlorosalicylic acid may be determined by gas phase chromatography on samples of the reaction mixture. The in situ yield of 3,5-dichlorosalicyclic acid at this point is about 95-98% of theoretical.

In carrying out the conversion of the 3,5-dichlorosalicyclic acid to 3,5,6-trichlorosalicylic acid, sulfur trioxide is added to the concentrated sulfuric acid to provide at least 4 moles of sulfur trioxide per mole of salicylic acid originally used. This is followed by the addition of a catalytic amount of iodine, about 20-500 milligrams, preferably about 100-150 milligrams, per mole of salicylic acid used. During the course of the addition of the sulfur trioxide, the temperature is prevented from exceeding 60° C. by external cooling, as necessary. Chlorine gas is then passed into the reaction mixture, at about 40°–60° C., until the uptake of chlorine ceases, as indicated by the initiation of bubbling at a gas bubbler device on the exhaust end of the reactor. The chlorination is carried out over about 0.5–2 hours, preferably about 0.5–0.75 hour. Again, the chlorination may optionally be carried out under pressure to increase the rate of reaction.

Upon completion of the chlorination, the reaction mixture is cooled to ambient conditions and then added to a mixture of ice and water to precipitate the 3,5,6-trichlorosalicylic acid as a solid. The solid may then be recovered by standard methods, such as filtration or centrifugation, washed with water and dried to obtain 3,5,6-trichlorosalicylic acid in a yield of about 78% of theoretical.

Optionally, the 3,5,6-trichlorosalicylic acid may be converted into an ester of formula (I) by methods described in the prior art.

Preferably, the mixture of ice, water, and 3,5,6-trichlorosalicylic acid is stirred with a mixture of a water-immiscible aromatic hydrocarbon solvent and an alcohol having 3 to 20 carbon atoms at a temperature of at least 60° C., preferably about 75°–100° C., to extract the 3,5,6-trichlorosalicylic acid into the organic phase.

Suitable water-immiscible aromatic hydrocarbons include benzene, toluene, xylene, chlorobenzene, nitrobenzene, and the like. The preferred solvent is xylene.

Suitable alcohols include n-propanol, n-butanol, n-pentanol, 2-ethylhexanol, dodecanol, octadecanol, eicosanol, and the like. The especially preferred alcohol is n-pentanol.

The two-phase liquid mixture is stirred for a period sufficient to extract essentially all of the 3,5,6-trichlorosaliculic acid into the organic phase and the mixture is allowed to settle. The organic phase is then separated from the aqueous phase. Preferably, the aqueous phase is extracted again with a fresh mixture of aromatic hydrocarbon solvent and alcohol. The organic phase is then separated from the aqueous phase and combined with the first organic extract.

The organic extract, containing 3,5,6-trichlorosalicylic acid, is treated with a catalytic amount of a suitable acid and heated at an elevated temperature to azeotrope water therefrom and obtain a solution of the compound of formula (I).

Suitable acids which may be used include sulfuric, methanesulfonic, p-toluenesulfonic, dodecylsulfonic, and phosphoric acid. The preferred acid is sulfuric acid.

The desired product can be recovered from the solution by stripping off the aromatic hydrocarbon solvent and excess alcohol, and distilling the residue.

The following examples illustrate the present invention. All parts are by weight unless otherwise indicated.

EXAMPLE 1

Preparation of 3,5,6-Trichlorosalicylic Acid

Sulfuric acid (96.0%; 505 grams) is charged into a round-bottomed Morton flask, equipped with a thermometer, stirrer, and sintered glass gas inlet tube, and cooled to 8°–10° C. Salicylic acid (115 grams; 0.83 mole) is added to the sulfuric acid and the mixture is stirred until the salicylic acid is completely dissolved. The resulting solution is cooled to 5° C. and chlorine gas is bubbled into it while maintaining the temperature at 5°–10° C. After about 45–50 minutes, 3,5-dichlorosalicylic acid starts to precipitate from solution. After chlorinating at 5°–10° for about 2 hours and 10 minutes beyond the onset of precipitation of 3,5-dichlorosalicylic acid, the reaction mixture is heated to 65°–70° C. and chlorination is continued for an additional 2 hours and 10 minutes at the elevated temperature. Chlorination is then discontinued, the reaction mixture is cooled to 10° C. and sulfur trioxide (197 mls; 4.53 moles) is carefully added thereto at a rate to keep the temperature at or below 55° C. Iodine (100 milligrams) is added to the reaction mixture and chlorination is resumed with the temperature at 50° C. After chlorinating for 35 minutes, a tan solid precipitates and chlorine uptake ceases. Analysis of the reaction mixture at this point shows that it is about 96% completed. The addition of chlorine is continued and the reaction mixture is stirred at 50° C. for an additional hour. The reaction mixture is then poured on a mixture of 2800 grams of cracked ice and water affording a yellow precipitate which is recovered by filtration, washed with water, and dried to obtain the desired product in a yield of 77.7% of theoretical.

EXAMPLE 2

Preparation of n-Pentyl 3,5,6-Trichlorosalicylate

The procedure of Example 1 is followed in every detail except that the mixture of cracked ice and yellow precipitate is extracted for one hour at 95° C. with 550 mls of a mixture of 1.75:1 parts by volume of xylene:n-pentanol. The mixture is allowed to settle, the organic layer is separated, and the aqueous layer is extracted again for one hour at 95° C. with 450 mls of xylene:n-pentanol mixture. Again the mixture is allowed to settle, the organic phase is separated and combined with the first organic extract. The total extract is charged into a 2-liter round-bottomed flask equipped with a Dean-Stark trap and a condenser. The contents are acidified with 96% sulfuric acid (14 mls) and refluxed for 16 hours while separating water by means of the Dean-Stark trap.

Vapor phase analysis of the reaction mixture, after refluxing for 16 hours, shows that it contains 238 grams of the desired product. This represents a yield which is 92% of theoretical based on the salicylic acid originally charged.

In the manner described above, substituting n-butanol for n-pentanol, similar yields are obtained.

EXAMPLE 3

The procedure of Example 2 is followed in every detail except that the chlorination of the salicylic acid is carried out at 20°–35° C. for a period of 6 hours and 12 minutes before elevating the temperature to 50° C. The overall yield of n-pentyl trichlorosalicylate from the salicylic acid is only 85% of theoretical.

This example illustrates the lower yield obtained by carrying out the mono chlorination of the salicylic acid at temperatures above the preferred temperature range of 5°–10° C.

EXAMPLE 4

The procedure of Example 3 is followed in every detail except that the chlorination of the salicylic acid is carried out at 20°–35° C. for a period of 8 hours and 45 minutes, and the chlorination in oleum to convert 3,5-dichlorosalicylic acid to 3,5,6-trichlorosalicylic is carried out at 70° C. for 1.5 hours. The overall yield of n-pentyl 3,5,6-trichlorosalicylate is only 76% of theoretical.

The above example illustrates the lower yield obtained by carrying out the chlorination in oleum at a temperature above 55° C.

EXAMPLE 5

The procedure of Example 3 is followed in every detail except that the chlorination of the salicylic acid is carried out at 20°–35° C. for a period of 6 hours and 30 minutes, and the chlorination at 50° C. is carried out for 6 hours and 18 minutes instead of one hour and 30 minutes. The overall yield of n-pentyl trichlorosalicylate, based on salicylic acid, is only 72% of theoretical.

This example illustrates the lower yield obtained by carrying out the chlorination at 50° C. for a prolonged period of time.

EXAMPLE 6

Oleum (4000 mls of 65%) is charged to a 12-liter flask and iodine (0.4 gram) is added to it. 3,5-Dichlorosalicylic acid (3000 grams; 14.5 moles) is added thereto with stirring at such a rate that the temperature does not exceed 70° C. Chlorine gas is then bubbled through the stirred mixture at 70° C. for 24 hours. The reaction mixture is then cooled to room temperature and drowned into a mixture of ice and water (about 20 kilograms). The resulting slurry is filtered, washed with water and dried at 60° C. to obtain 2207 grams (63.5% of theoretical) of 3,5,6-trichlorosalicylic acid.

This experiment illustrates the lower yield obtained when the chlorination of 3,5-dichlorosalicylic acid is carried out at the elevated temperature for a long period of time.

EXAMPLE 7

The procedure of Example 2 is followed, substituting toluene for the xylene, and refluxing the reaction mixture for 60 hours while separating water by means of the Dean-Stark trap. A similar yield of n-pentyl 3,5,6-trichlorosalicylate is obtained.

In the manner described above, increasing the amount of 96% sulfuric acid to 28 mls reduces the reaction time to 24 hours.

We claim:

1. A process for preparing 3,5,6-trichlorosalicylic acid comprising:
   (1) contacting a solution of salicylic acid in concentrated sulfuric acid with chlorine at a temperature below 35° C. until essentially all of the salicylic acid is converted into monochlorosalicylic acid; further converting the monochlorosalicylic acid to 3,5-dichlorosalicylic acid by contacting it with chlorine at a temperature in the range 50°–75° C.,
   (2) adding to the product solution of 3,5-dichlorosalicylic acid about 4 moles of sulfur trioxide for each mole of salicylic acid that was used in step (1), with the temperature of the solution at or below 55° C. during the addition of sulfur trioxide.
   (3) adding a catalytic amount of iodine to the solution obtained by step (2),
   (4) contacting the solution obtained in step (3) with gaseous chlorine while maintaining the solution temperature about 40°–60° C., until absorption of chlorine by the solution has ceased.
   (5) cooling the reaction mixture from step (4) to ambient temperature and adding the cooled reaction mixture to water at 0° C., thereby precipitating 3,5,6-trichlorosalicylic acid as a solid.

2. The process of claim 1 wherein the gaseous chlorine is contacted with the solution of salicylic acid at a temperature of 5°–10° C.; the 5-chlorosalicylic acid is converted to 3,5-dichlorosalicylic acid by contact with chlorine at 65°–70° C.; 100–150 milligrams of iodine per mole of the salicylic acid charged in step (1) is added in step (3); and gaseous chlorine is contacted with the reaction mixture at about 47°–54° C. in step (4).

3. A process for preparing esters of 3,5,6-trichlorosalicylic acid represented by the formula

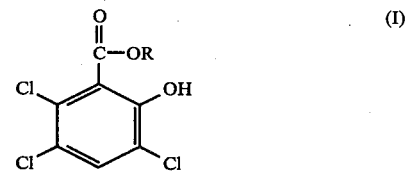

in which R represents alkyl ($C_3$–$C_{20}$) further comprising:
   (1) extracting the water containing precipitated 3,5,6-trichlorosalicylic acid prepared as defined in claim 1 with a mixture of a water-immiscible hydrocarbon solvent and an alcohol having 3 to 20 carbon atoms at a temperature of at least 60° C. to form a two-phase liquid mixture with the 3,5,6-trichlorosalicylic acid in the organic phase,
   (2) separating the organic phase from the aqueous phase,
   (3) adding a catalytic amount of a suitable acid to the separated organic phase and,
   (4) distilling the water azeotrope from the mixture leaving a solution containing the compound of formula (I).

4. The process of claim 3 wherein the alcohol used for the defined extraction contains 2–8 carbon atoms and the extraction temperature is about 75°–100° C. and a catalytic amount of concentrated sulfuric acid is added to the organic phase after separation from the water phase.

5. The process of claim 4 wherein the mixture of organic solvents used for extraction consists of about 1.5–2.0 parts by volume of xylene and about one part by volume of n-pentanol and the extraction temperature is about 90°–100° C.

6. The process of claim 4 wherein the mixture of organic solvents used for extraction consists of about 1.5–2.0 parts by volume of toluene and about one part by volume of n-pentanol and the extraction temperature is about 70°–100° C.

* * * * *